United States Patent
Vogt

(10) Patent No.: US 9,457,124 B2
(45) Date of Patent: Oct. 4, 2016

(54) PASTE-LIKE BONE CEMENT

(71) Applicant: HERAEUS MEDICAL GMBH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 62 days.

(21) Appl. No.: 13/945,017

(22) Filed: Jul. 18, 2013

(65) Prior Publication Data
US 2014/0024739 A1    Jan. 23, 2014

(30) Foreign Application Priority Data
Jul. 20, 2012 (DE) .................. 10 2012 014 418

(51) Int. Cl.
| | |
|---|---|
| A61K 6/083 | (2006.01) |
| A61K 6/00 | (2006.01) |
| A61L 24/00 | (2006.01) |
| A61L 27/44 | (2006.01) |
| A61L 24/02 | (2006.01) |

(52) U.S. Cl.
CPC ........ *A61L 24/0073* (2013.01); *A61L 24/0089* (2013.01); *A61L 24/02* (2013.01); *A61L 27/446* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 3,654,161 A * | 4/1972 | Geus | ...... | H01F 1/063 252/62.51 R |
| 4,015,945 A | 4/1977 | Frankel et al. | | |
| 4,437,836 A | 3/1984 | Schmitz-Josten et al. | | |
| 4,499,251 A * | 2/1985 | Omura | ...... | A61L 24/06 106/35 |
| 4,515,930 A * | 5/1985 | Omura | ...... | C08F 230/02 106/35 |
| 4,525,493 A * | 6/1985 | Omura | ...... | A61L 24/06 106/35 |
| 4,539,382 A * | 9/1985 | Omura | ...... | C07F 9/091 106/35 |
| 4,624,971 A * | 11/1986 | van Tao | ...... | B82Y 30/00 428/404 |
| 4,650,847 A * | 3/1987 | Omura | ...... | C07F 9/091 106/35 |
| 4,820,744 A * | 4/1989 | Kubota | ...... | A61K 6/083 522/10 |
| 4,910,259 A * | 3/1990 | Kindt-Larsen | ...... | A61L 24/001 523/116 |
| 5,374,664 A * | 12/1994 | Zalsman | ...... | A61K 6/0023 523/118 |
| 5,521,243 A * | 5/1996 | Minghetti | ...... | C04B 26/06 524/437 |
| 5,567,745 A * | 10/1996 | Minghetti | ...... | C04B 26/06 523/202 |
| 5,681,872 A * | 10/1997 | Erbe | ...... | A61B 17/866 106/35 |
| 5,705,552 A * | 1/1998 | Minghetti | ...... | C04B 26/06 524/437 |
| 5,747,154 A * | 5/1998 | Minghetti | ...... | C04B 26/06 428/327 |
| 5,795,922 A * | 8/1998 | Demian | ...... | A61L 24/001 424/419 |
| 5,914,356 A * | 6/1999 | Erbe | ...... | A61K 6/083 106/35 |
| 5,985,972 A * | 11/1999 | Minghetti | ...... | C04B 26/06 524/430 |
| 6,177,499 B1 * | 1/2001 | Minghetti | ...... | C04B 26/06 524/430 |
| 6,447,907 B1 * | 9/2002 | Wolter | ...... | A61K 6/0008 428/402 |
| 6,593,394 B1 * | 7/2003 | Li | ...... | A61K 6/033 424/422 |
| 8,389,598 B2 * | 3/2013 | Saimi | ...... | A61K 6/083 106/35 |
| 8,642,064 B2 | 2/2014 | Schnabelrauch et al. | | |
| 8,865,777 B2 | 10/2014 | Vogt et al. | | |
| 2002/0022677 A1 | 2/2002 | Teramae et al. | | |
| 2003/0017311 A1 * | 1/2003 | Garitano | ...... | B41M 5/035 428/195.1 |
| 2003/0086332 A1 | 5/2003 | Jonsson | | |
| 2004/0229971 A1 * | 11/2004 | Rossi | ...... | A61K 6/10 523/109 |

(Continued)

FOREIGN PATENT DOCUMENTS

| | | |
|---|---|---|
| CA | 2789793 | 9/2011 |
| CA | 2742537 A1 | 12/2011 |
| CN | 1886160 A | 12/2006 |
| CN | 102333552 A | 1/2012 |

(Continued)

OTHER PUBLICATIONS

Osteoconductivity and Bone Bonding Strength of High and Low Viscous Bioactive Bone Cements, Koyayashi et al., Journal of Biomedical Materials Research Dec. 1998; 48(3):265-276. DOI: 10.1002/(SICI)1097-4636(1999)48:3<265::AID-JBM10>3.0. CO;2-0.*

(Continued)

*Primary Examiner* — Peter A Salamon
(74) *Attorney, Agent, or Firm* — Norris McLaughlin & Marcus P.A.

(57) ABSTRACT

Paste containing at least one monomer for radical polymerization, at least one polymer that is soluble in said at least one monomer for radical polymerization, and at least one filling agent that is poorly soluble or insoluble in said at least one monomer for radical polymerization, wherein the filling agent is a particulate inorganic filling agent possessing a BET surface of at least 40 m$^2$/g; kit comprising pastes A and B which, when mixed, form paste C, which pastes are useful for mechanical fixation of articular endoprostheses, for covering skull defects, for filling bone cavities, for femuroplasty, for vertebroplasty, for kyphoplasty, for the manufacture of spacers or for the production of carrier materials for local antibiotics therapy, as well as a form body produced from the pastes.

11 Claims, No Drawings

(56) References Cited

U.S. PATENT DOCUMENTS

| | | |
|---|---|---|
| 2006/0030637 A1 | 2/2006 | Mitra et al. |
| 2007/0196509 A1* | 8/2007 | Riman .................. A61K 33/42 424/602 |
| 2007/0260325 A1* | 11/2007 | Wenz .................... A61L 24/001 623/23.62 |
| 2009/0105144 A1 | 4/2009 | Vogt et al. |
| 2009/0105366 A1 | 4/2009 | Vogt et al. |
| 2009/0105367 A1 | 4/2009 | Vogt et al. |
| 2010/0209695 A1* | 8/2010 | Cho ....................... C04B 26/02 428/323 |
| 2011/0028589 A1* | 2/2011 | Saimi ..................... A61K 6/083 523/115 |
| 2011/0183932 A1 | 7/2011 | Vogt et al. |
| 2011/0313078 A1 | 12/2011 | Vogt et al. |
| 2012/0022542 A1* | 1/2012 | Boger .................... A61L 27/46 606/94 |
| 2012/0034281 A1 | 2/2012 | Kaneko et al. |
| 2012/0035296 A1* | 2/2012 | Nakamura .......... A61L 24/0089 523/116 |
| 2012/0046385 A1* | 2/2012 | Nakamura .......... A61L 24/0089 523/116 |
| 2014/0024739 A1* | 1/2014 | Vogt ..................... A61L 27/446 523/116 |

FOREIGN PATENT DOCUMENTS

| | | |
|---|---|---|
| CN | 102405038 | 4/2012 |
| DE | 10 2007 050 763 A | 4/2009 |
| DE | 10 2007 052 116 A | 4/2009 |
| DE | 10 2007 050 762 A | 5/2009 |
| DE | 10 2010 005 956 A1 | 7/2011 |
| DE | 10 2010 024 653 A1 | 12/2011 |
| EP | 0 674 888 A | 10/1995 |
| EP | 2 550 980 A2 | 1/2013 |
| JP | 2001-302429 A | 10/2001 |
| JP | 2003 181270 A | 7/2003 |
| JP | 2007054369 A | 3/2007 |
| JP | 2009-101159 A | 5/2009 |
| JP | 2012-040213 A | 3/2012 |
| JP | 2013-148476 A | 8/2013 |
| WO | 01/49327 A2 | 7/2001 |
| WO | 2004/103420 A1 | 12/2004 |
| WO | 2011/068481 A1 | 6/2011 |
| WO | 2011/141889 A1 | 11/2011 |

OTHER PUBLICATIONS

English Translation of Chinese Office Action dated Sep. 23, 2014.
Cabot Corp.: Product Data Sheet for Cab-O-Sil(R) TS-610, Tuscola (USA), 2002.
Floerke, O.W., "Silica", Ullmanns Encyclopedia of Industrial Chemistry, Weinheim: Wiley-VCH Verlan, vol. 32, p. 421-507, 2012.
Canadian Office Action dated Jun. 29, 2015.
Notice of Decision dated Aug. 18, 2015.
English Translation of Notice of Decision dated Aug. 18, 2015.
English Translation of Japanese Office Action dated Sep. 9, 2014.
Examination Report dated Oct. 17, 2014.
Canadian Office Action dated Oct. 22, 2014.
Canadian Office Action for corresponding Canadian Patent Application No. 2,820,546 issued Mar. 4, 2016.
XP-002753085, Database WPI, Dec. 2, 2004; Thomson Scientific, London.
European Search Report dated Feb. 5, 2016.
Chinese Office Action dated Dec. 28, 2015.
English Translation of Chinese Office Action dated Dec. 28, 2015.

* cited by examiner

PASTE-LIKE BONE CEMENT

The present invention relates to a paste, a kit, the use of a paste or of a paste produced from a kit for mechanical fixation of articular endoprostheses, for covering skull defects, for filling bone cavities, for femuroplasty, for vertebroplasty, for kyphoplasty, for the manufacture of spacers or for the production of carrier materials for local antibiotics therapy, as well as a form body.

BACKGROUND OF THE INVENTION

Conventional polymethylmethacrylate bone cements (PMMA bone cements) have been known for decades and are based on the ground-breaking work of Sir Charnley (Charnley, J.: "*Anchorage of the femoral head prosthesis of the shaft of the femur*"; J. Bone Joint Surg. 42 (1960) 28-30). The basic structure of PMMA bone cements has remained the same ever since. PMMA bone cements consist of a liquid monomer component and a powder component. The monomer component generally contains (i) the monomer, methylmethacrylate, and (ii) an activator (e.g. N,N-dimethyl-p-toluidine) dissolved therein. The powder component comprises (i) one or more polymers that are made by polymerisation, preferably by suspension polymerisation, based on methylmethacrylate and co-monomers, such as styrene, methylacrylate or similar monomers, (ii) a radio-opaquer, and (iii) an initiator, (e.g. dibenzoylperoxide). Mixing the powder component and the monomer component, the polymers of the powder component in the methylmethacrylate swell which generates a dough that can be shaped plastically. Simultaneously, the activator, N,N-dimethyl-p-toluidine, reacts with dibenzoylperoxide which disintegrates and forms radicals in the process. The radicals thus formed trigger the radical polymerisation of the methylmethacrylate. Upon advancing polymerisation of the methylmethacrylate, the viscosity of the cement dough increases until the cement dough solidifies and thus is cured.

The essential disadvantage of the previous PMMA bone cements for the medical user is that the user needs to mix the liquid monomer component and the powder component in a mixing system or in crucibles right before applying the cement. Mixing errors can easily occur in the process and adversely affect the quality of the cement. Moreover, the components must be mixed rapidly. In this context, it is important to mix all of the cement powder and monomer component without forming lumps and prevent the introduction of air bubbles during the mixing process. Unlike manual mixing, the use of vacuum mixing systems prevents the formation of air bubbles in the cement dough to a large extent. Examples of mixing systems are disclosed in patent specifications U.S. Pat. No. 4,015,945, EP-A-0 674 888, and JP-A-2003181270. However, vacuum mixing systems necessitate an additional vacuum pump and are therefore relatively expensive. Moreover, depending on the type of cement concerned, a certain waiting time is required after mixing the monomer component and the powder component until the cement dough is tack-free and can be applied. Because of the large variety of errors that can occur while mixing conventional PMMA bone cements, appropriately trained personnel is required for this purpose. The corresponding training is associated with considerable expenses. Moreover, mixing of the liquid monomer component and the powder component is associated with exposure of the user to monomer vapours and particles released from the powder-like cement.

Pasty polymethylmethacrylate bone cements containing a methacrylate monomer for radical polymerisation, a polymer that is soluble in said methacrylate monomer, and a particulate polymer that is insoluble in said methacrylate monomer have been described as an alternative to the conventional powder-liquid polymethylmethacrylate bone cements in unexamined German patent applications DE-A-10 2007 052 116, DE-A-10 2007 050 762, and DE-A-10 2007 050 763. Paste-like polymethylmethacrylate bone cements of this type can be present as one-component systems (in this case, the paste contains all components required for curing, in particular an activatable radical initiator, e.g. a photoinitiator or a photoinitiator system) or as two-component systems (in this case, the system comprises two pre-mixed pastes that are stable on storage and one of which comprises a radical polymerisation initiator and the other comprises a polymerisation activator). Referring to two-component systems, a distinction is made between a "symmetrical system" (in this case both pastes contain a particulate polymer that is insoluble in the methacrylate monomer) and "non-symmetrical systems" (in this case, only one of the two pastes contains a particulate polymer that is insoluble in the methacrylate monomer).

As a result of the selected composition, the bone cement produced from the pastes described above possesses sufficiently high viscosity and cohesion in order to withstand the pressure from bleeding until it is fully cured. Owing to the advancing polymerisation, the paste is cured while the methacrylate monomers are consumed.

Aside from at least one monomer for radical polymerisation and at least one polymer dissolved therein, the pasty polymethylmethacrylate bone cements disclosed in DE-A-10 2007 052 116, DE-A-10 2007 050 762, and DE-A-10 2007 050 763 contain polymer particles that are insoluble in said monomer. Said insoluble polymer particles are a filling agent. Said filling agent has a significant influence on the viscosity of the cement pastes. The polymer particles are essential for the processing properties to ensure that the cement pastes show as little restoring motion as possible during the application phase of the shaping process. This allows the cement pastes to be moulded into any shape during the processing phase such as is generally known for conventional polymethylmethacrylate bone cements that are based on the mixing of polymer powder and monomer liquid.

The production of cross-linked polymer particles that are insoluble in methacrylate monomers is relatively laborious and therefore expensive. For this reason, it is desirable to identify an alternative, inexpensive particulate material which, after admixture into mixtures of methacrylate monomers and polymers dissolved therein, yields pastes that show only minimal elastic resilience after shaping much like cross-linked polymer particles.

However, one problem is that the cross-linked polymer particles used thus far also contributed to the mechanical stability of the cured pasty cements. It is therefore important to identify an alternative filling agent which not only ensures that the pastes have the requisite processing properties, but also does not adversely affect the mechanical parameters of the cured cements such that the mechanical stability requirements of ISO 5833 are met.

SUMMARY

The present invention was based on the object to overcome the disadvantages of prior art bone cement systems that are based on pastes, in particular with regard to the two-component systems described above.

In particular, the present invention was based on the object to provide a bone cement paste, in particular a bone cement paste based on a two-component system, which can be produced from less expensive starting materials than bone cement pastes known according to the prior art, but still features the same processing properties as the pastes according to the prior art.

A contribution to meeting the objects specified above is made by a paste containing at least one monomer for radical polymerisation, at least one polymer that is soluble in said monomer for radical polymerisation, and at least one filling agent that is poorly soluble or insoluble in said at least one monomer for radical polymerisation, whereby the filling agent is a particulate inorganic filling agent with a BET surface of at least 40 $m^2/g$, particularly preferably of at least 200 $m^2/g$, and most preferably of at least 300 $m^2/g$.

The invention is based on finding that bone cement pastes that can be formed and shaped well can be produced through the use of particulate inorganic filling agents possessing a BET surface of at least 40 $m^2/g$, which was a surprise considering the previously known pasty polymethylmethacrylate bone cements. It is surprising that the hitherto customary cross-linked polymer particles that are insoluble in methacrylate monomers can be replaced fully or partly by particulate inorganic filling agents that possess a BET surface of at least 40 $m^2/g$. Inorganic filling agents of this type are markedly less expensive than cross-linked polymer particles and can therefore be used to economic advantage in the production of pasty polymethylmethacrylate bone cements.

Surprisingly, it was feasible to produce cement pastes that met the mechanical requirements of ISO 5833 after curing despite the use of inorganic particles instead of cross-linked polymer particles.

It is particularly advantageous to use particulate inorganic filling agents possessing a BET surface of at least 40 $m^2/g$ to produce pasty bone cement pastes for kyphoplasty and vertebroplasty that contain a high radiopaquer fraction and have a processing time of at least 15 minutes.

As a matter of principle, the paste according to the invention can be a one-component system of the type described above or can be obtained through mixing the two pastes of a two-component system of the type described above.

DETAILED DESCRIPTION

The paste according to the invention contains, as a component, at least one monomer for radical polymerisation, whereby this is preferably a methacrylate monomer, in particular a methacrylate monomer that is liquid at a temperature of 25° C. and a pressure of 1,013 hPa.

Preferably, the monomer for radical polymerisation is not a bisphenol A-derived methacrylic acid ester.

Preferably, the methacrylate monomer is a methacrylic acid ester. Preferably, the methacrylic acid ester is a monofunctional methacrylic acid ester. Preferably, said substance is hydrophobic. The use of hydrophobic monofunctional methacrylic acid esters allows later increases in bone cement volume due to the uptake of water and thus damage to the bone to be prevented. According to a preferred embodiment, the monofunctional methacrylic acid ester is hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The esters preferably are alkyl esters. According to the invention, cycloalkyl esters are also included in alkyl esters. According to a preferred embodiment, the alkyl esters are esters of methacrylic acid and alcohols comprising 1 to 20 carbon atoms, more preferably 1 to 10 carbon atoms, even more preferably 1 to 6 carbon atoms, and particularly preferably 1 to 4 carbon atoms. The alcohols can be substituted or non-substituted and preferably are non-substituted. Moreover, the alcohols can be saturated or unsaturated and preferably are saturated.

The monomer for radical polymerisation used according to the invention preferably has a molar mass of less than 1,000 g/mol. This also comprises monomers for radical polymerisation that are components of a mixture of monomers, whereby at least one of the monomers for radical polymerisation of the mixture of monomers has a defined structure with a molar mass of less than 1,000 g/mol.

The monomer for radical polymerisation is preferably characterised in that an aqueous solution of the monomer for radical polymerisation has a pH in the range of 5 to 9, preferably in the range of 5.5 to 8.5, even more preferably in the range of 6 to 8, and particularly preferably in the range of 6.5 to 7.5.

According to a particularly preferred embodiment, the methacrylate monomer is a methacrylic acid methylester, methacrylic acid ethylester or a mixture of said two monomers.

Preferably, the paste according to the invention contains an amount of the monomer for radical polymerisation in a range of 15 to 85% by weight, more preferably 20 to 70% by weight, even more preferably 25 to 60% by weight, and particularly preferably 25 to 50% by weight, each relative to the total weight of the paste according to the invention.

The paste according to the invention contains, as further component, at least one polymer that is soluble in said at least one monomer for radical polymerisation. According to the invention, a polymer is soluble in the polymerisable monomer, if at least 10 g/l, preferably at least 25 g/l, more preferably at least 50 g/l, and particularly preferably at least 100 g/l of the polymer dissolve in said polymerisable monomer. The polymer that is soluble in the polymerisable monomer can be a homopolymer or a copolymer. Said soluble polymer preferably is a polymer with a mean (by weight) molar mass of at least 150,000 g/mol. The soluble polymer can, for example, be a polymer or copolymer of a methacrylic acid ester. According to a particularly preferred embodiment, the at least one soluble polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), poly(styrene-co-methylmethacrylate), and a mixture of at least two of said polymers.

The amount of the polymer that is soluble in said monomer for radical polymerisation that is present in the paste usually is in a range of 1 to 85% by weight, relative to the total weight of the paste according to the invention.

Moreover, the paste according to the invention contains at least one filling agent that is poorly soluble or insoluble in the at least one monomer for radical polymerisation, whereby the filling agent is a particulate inorganic filling agent possessing a BET surface of at least 40 $m^2/g$, particularly preferably of at least 200 $m^2/g$, and most preferably of at least 300 $m^2/g$.

The BET measurement is an analytical procedure for characterisation of the surface of solids by means of gas adsorption. Said determination method is described in DIN ISO 9277:2003-05 (Determination of the specific surface of solids by gas adsorption according to the BET method.

According to a preferred refinement of the paste according to the invention, the particulate inorganic filling agent is a particulate inorganic filling agent that comprises hydroxy groups that are bound covalently to the particles. Said hydroxy groups that are arranged on the surface of the particles allow hydrogen bonds between the filling agent particles to form, which can be released reversibly through the action of mechanical or thermal energy. Particulate inorganic filling agents comprising silanol groups (HO—Si groups) are particularly preferred.

In this context, according to the invention, it is preferred that the particulate inorganic filling agent is selected from the group consisting of pyrogenic silicon dioxide, pyrogenic metal-silicon mixed oxides, titanium dioxide, bentonite, montmorillonite, and a mixture of at least two of these substances.

Moreover, it is also feasible to use pyrogenic silicon dioxide made hydrophobic. The hydrophobic silicon dioxide can be produced according to the prior art through treating pyrogenic silicon dioxide with dialkyldichlorosilanes (e.g. dimethyldichlorosilane).

Pyrogenic silicon dioxide with a BET surface of at least 40 $m^2/g$, particularly preferably of 200 $m^2/g$, and most preferably of 300 $m^2/g$ is particularly preferred as particulate inorganic filling agent. Said pyrogenic silicon dioxide is commercially available by the brand name of Aerosil® having specific BET surfaces of 50 $m^2/g$, 90 $m^2/g$, 200 $m^2/g$, and 380 $m^2/g$. Mixed oxides of silicon and metal oxides instead of pyrogenic silicon dioxide are well-suited as well. Mixed oxides of silicon and iron are well-suited as well.

The amount of the particulate inorganic filling agent that is present in the paste according to the invention usually is in a range of 0.5 to 25% by weight, particularly preferably from 1 to 20% by weight, and most preferably in a range of 5 to 15% by weight, each relative to the total weight of the paste. Aside from the particulate inorganic filling agent described above, the paste according to the invention can contain certain amounts of another filling agent, if applicable, for example the cross-linked polymer particles that are known according to the prior art, whereby the weight ratio of particulate inorganic filling agent to cross-linked polymer particles in this case preferably is at least 1:15 (i.e. at least approx. 6% by weight particulate inorganic filling agent relative to the total amount of filling agent), particularly preferably is at least 1:1 (i.e. at least 50% by weight particulate inorganic filling agent relative to the total amount of filling agent).

Preferably, the paste according to the invention is tack-free in accordance with ISO 5833 no later than 15 minutes after being produced.

Moreover, the paste according to the invention can contain at least one polymerisation initiator (which preferably is soluble in the monomer for radical polymerisation), at least one polymerisation accelerator (which preferably is soluble in the monomer for radical polymerisation), at least one polymerisation co-accelerator, if applicable, or at least one polymerisation initiator, at least one polymerisation accelerator, and, if applicable, at least one polymerisation co-accelerator.

In the case of a one-component system, the polymerisation initiator preferably is an activatable polymerisation initiator, e.g. a photoinitiator that is dissolved or suspended in the paste or a photoinitiator system that is dissolved or suspended in the paste. It is feasible just as well to provide an initiator or initiators where it/they are temporarily in contact with the paste, for example in a container part, a dosing facility or a transport cannula. Moreover, in a one-component system, the paste according to the invention can also contain an electrically conductive radio-opaquer aside from the activatable polymerisation initiator. Particles made of cobalt, iron, NdFeB, SmCo, cobalt-chromium steel, zirconium, hafnium, titanium, titanium-aluminium-silicon alloys, and titanium-niobium alloys having a particle size of 0.5-500 μm are particularly well-suited in this context. It is feasible to induce eddy currents in said electrically conductive radio-opaquer through alternating magnetic fields with a frequency in the range of 500 Hz to 50 kHz which cause the radio-opaquer to heat up. Due to heat transmission, the initiator is heated as well and induced to thermally disintegrate.

In the case of a paste according to the invention that was obtained through combining two pastes of a two-component system, said paste preferably contains at least one polymerisation initiator (that was contained in the one paste of the two-component system) and at least one polymerisation accelerator (that was contained in the other paste of the two-component system).

Conceivable as polymerisation initiator are, in particular, peroxides and barbituric acid derivatives, whereby preferably at least 1 g/l, more preferably at least 3 g/l, even more preferably at least 5 g/l, and particularly preferably at least 10 g/l of the peroxides and barbituric acid derivatives can dissolve(s) in the polymerisable monomer at a temperature of 25° C.

According to the invention, a peroxide is understood to mean compounds that contain at least one peroxo group (—O—O—). The peroxide preferably comprises no free acid groups. The peroxide can be an inorganic peroxide or an organic peroxide, such as, for example, a toxicologically acceptable hydroperoxide. According to a particularly preferred embodiment, the peroxide is selected from the group consisting of cumene-hydroperoxide, 1,1,3,3-tetramethylbutyl-hydroperoxide, t-butyl-hydroperoxide, t-amyl-hydroperoxide, di-isopropylbenzen-mono-hydroperoxide, and a mixture of at least two of these substances.

The barbituric acid derivative preferably is a barbituric acid derivative selected from the group consisting of 1-mono-substituted barbiturates, 5-mono-substituted barbiturates, 1,5-di-substituted barbiturates, and 1,3,5-tri-substituted barbiturates. According to a particular refinement of the paste according to the invention, the barbituric acid derivative is selected from the group consisting of 1,5-di-substituted barbiturates and 1,3,5-tri-substituted barbiturates.

There is no limitation with regard to the type of substituents on the barbituric acid. The substituents can, for example, be aliphatic or aromatic substituents. In this context, alkyl, cycloalkyl, allyl or aryl substituents can be preferred. The substituents can also include hetero atoms. In particular, the substituents can be thiol substituents. Accordingly, 1,5-disubstituted thiobarbiturates or 1,3,5-trisubstituted thiobarbiturates can be preferred. According to a preferred embodiment, the substituents each have a length of 1 to 10 carbon atoms, more preferably a length of 1 to 8 carbon atoms, and particularly preferably a length in the range of 2 to 7 carbon atoms. According to the invention, barbiturates bearing one substituent each at position 1 and position 5 or a substituent at positions 1, 3, and 5 are preferred. According to another preferred embodiment, the barbituric acid derivative is a 1,5-disubstituted barbiturate or a 1,3,5-trisubstituted barbiturate.

According to a particularly preferred embodiment, the barbituric acid derivative is selected from the group consisting of 1-cyclohexyl-5-ethyl-barbituric acid, 1-phenyl-5-ethyl-barbituric acid, and 1,3,5-trimethyl-barbituric acid.

Heavy metal compounds selected from the group consisting of heavy metal salts and heavy metal complexes are preferred as polymerisation accelerator.

Heavy metal compounds that are preferred according to the invention are selected from the group consisting of copper(II) hydroxide, copper(II) methacrylate, copper(II) acetylacetonate, copper(II)-2-ethyl-hexanoate, cobalt(II) hydroxide, cobalt(II)-2-ethyl-hexanoate, basic copper(II) carbonate, iron(II)-2-ethyl-hexanoate, iron(III)-2-ethyl-hexanoate, and a mixture of at least two of these substances.

According to another refinement of the paste according to the invention, the polymerisation accelerator is selected from the group consisting of N,N-dimethyl-p-toluidine, N,N-bishydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, pyromellitic acid diimide, and a mixture of at least two of these substances.

Another advantageous refinement of the invention consists of the use, as polymerisation accelerator, of combinations of heavy metal salts and at least one member of the group consisting of N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, and pyromellitic acid diimide. Combinations of two and combinations of three different polymerisation accelerators in this context are included in the scope of the invention.

An advantageous refinement of the invention consists of the paste according to the invention containing at least one polymerisation co-accelerator, if applicable, whereby tertiary amines and amidines are preferred as polymerisation co-accelerators, and whereby N,N-dimethyl-p-toluidine, N,N-bis-hydroxyethyl-p-toluidine, N,N-dimethyl-aniline, 1,8-diazabicyclo[5.4.0-]undec-7-ene, and 1,5-diazabicyclo (4.3.0)-non-5-ene are particularly preferred as co-accelerators.

The paste according to the invention can contain a (total) amount of up to 10% by weight, relative to the total weight of the paste according to the invention, of the polymerisation initiator, polymerisation accelerator, polymerisation co-accelerator or polymerisation accelerator and polymerisation co-accelerator.

The paste according to the invention can contain further ingredients aside from the components specified above.

According to a preferred embodiment of the paste according to the invention, said paste can contain at least one radio-opaquer. The radio-opaquer can be a common radio-opaquer in this field. Suitable radio-opaquers can be soluble or insoluble in the monomer for radical polymerisation. The radio-opaquer is preferably selected from the group consisting of metal oxides (such as, for example, zirconium oxide), barium sulfate, toxicologically acceptable heavy metal particles (such as, for example, tantalum), ferrite, magnetite (supramagnetic magnetite also, if applicable), and biocompatible calcium salts. Said radio-opaquers preferably have a mean particle diameter in the range of 10 nm to 500 µm. Moreover, conceivable radio-opaquers also include esters of 3,5-bis(acetamido)-2,4,6-triiodobenzoic acid, gadolinium compounds, such as gadolinium chelate involving the esters of 1,4,7,10-tetraazacyclododecan-1,4,7,10-tetraacetic acid (DOTA). The concentration of radiopaquer, in particular the concentration of zirconium dioxide, that is present in the paste according to the invention can, for example, be in a range of 3 to 30% by weight.

According to a further preferred embodiment, the paste according to the invention can contain at least one colourant. The colourant can be a common colourant in this field and preferably can be a food colourant. Moreover, the colourant can be soluble or insoluble in the at least one monomer for radical polymerisation. According to a particularly preferred embodiment, the colourant is selected from the group consisting of E101, E104, E132, E141 (chlorophyllin), E142, riboflavin, and lissamine green. According to the invention, the term, colourant, shall also include colour varnishes, such as, for example, colour varnish green, the aluminium salt of a mixture of E104 and E132.

According to a further preferred embodiment, the paste according to the invention can contain at least one pharmaceutical agent. The at least one pharmaceutical agent can be present in the paste according to the invention in dissolved or suspended form. The pharmaceutical agent can preferably be selected from the group consisting of antibiotics, antiphlogistic agents, steroids, hormones, growth factors, bisphosphonates, cytostatic agents, and gene vectors. According to a particularly preferred embodiment, the at least one pharmaceutical agent is an antibiotic. Preferably, the at least one antibiotic is selected from the group consisting of aminoglyoside antibiotics, glycopeptide antibiotics, lincosamide antibiotics, gyrase inhibitors, carbapenems, cyclic lipopeptides, glycylcyclines, oxazolidones, and polypeptide antibiotics. According to a particularly preferred embodiment, the at least one antibiotic is a member selected from the group consisting of gentamicin, tobramycin, amikacin, vancomycin, teicoplanin, dalbavancin, lincosamine, clindamycin, moxifloxacin, levofloxacin, ofloxacin, ciprofloxacin, doripenem, meropenem, tigecycline, linezolide, eperezolide, ramoplanin, metronidazole, timidazole, omidazole, and colistin, as well as salts and esters thereof. Accordingly, the at least one antibiotic can be selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, and moxifloxacin. The at least one antiphlogistic agent is preferably selected from the group consisting of non-steroidal antiphlogistic agents and glucocorticoids. According to a particularly preferred embodiment, the at least one antiphlogistic agent is selected from the group consisting of acetylsalicylic acid, ibuprofen, diclofenac, ketoprofen, dexamethasone, prednisone, hydrocortisone, hydrocortisone acetate, and fluticasone. The at least one hormone is preferably selected from the group consisting of serotonin, somatotropin, testosterone, and estrogen. Preferably, the at least one growth factor is selected from the group consisting of fibroblast growth factor (FGF), transforming growth factor (TGF), platelet derived growth factor (PDGF), epidermal growth factor (EGF), vascular endothelial growth factor (VEGF), insulin-like growth factors (IGF), hepatocyte growth factor (HGF), bone morphogenetic protein (BMP), interleukin-1B, interleukin 8, and nerve growth factor. The at least one cytostatic agent is preferably selected from the group consisting of alkylating agents, platinum analogues, intercalating agents, mitosis inhibitors, taxanes, topoisomerase inhibitors, and antimetabolites.

The at least one bisphosphonate is preferably selected from the group consisting of zoledronate and aledronate.

According to a further preferred embodiment, the paste according to the invention can contain at least one biocompatible elastomer. Preferably, the biocompatible elastomer is particulate. Preferably, the biocompatible elastomer is soluble in the at least one monomer for radical polymerisation. The use of butadiene as biocompatible elastomer has proven to be particularly well-suited.

According to a further preferred embodiment, the paste according to the invention can contain at least one monomer having adsorption groups. The adsorption group can, for example, be an amide group. Accordingly, the monomer with adsorption group can, for example, be methacrylic acid amide. Using at least one monomer with adsorption groups would allow the binding of the bone cement to articular endoprostheses to be influenced in a targeted manner.

According to a further preferred embodiment, the paste according to the invention can contain at least one stabiliser. The stabiliser should be suitable to prevent spontaneous polymerisation of the monomers for radical polymerisation that are contained in the paste. Moreover, the stabiliser should not undergo interfering interactions with the other ingredients contained in the paste according to the invention. Stabilisers of said type are known according to the prior art. According to a preferred embodiment, the stabiliser is 2,6-di-tert-butyl-4-methylphenol and/or 2,6-di-tertbutyl-phenol.

A kit comprising a paste A and a paste B also makes a contribution to a solution meeting the object specified above,
whereby
(a) paste A contains
 (a1) at least one monomer for radical polymerisation;
 (a2) at least one polymer that is soluble in (a1); and
 (a3) at least one polymerisation initiator;
(b) paste B contains
 (b1) at least one monomer for radical polymerisation;
 (b2) at least one polymer that is soluble in (b1); and
 (b3) at least one polymerisation accelerator;
and whereby at least one of the pastes A and B contains as component (a4) and/or (b4) at least one filling agent that is poorly soluble or insoluble in (a1)) and/or (b1), respectively, whereby the filling agent is a particulate inorganic filling agent possessing a BET surface of at least 40 m²/g, particularly preferably of at least 200 m²/g, and most preferably of at least 300 m²/g.

According to the invention, a kit shall be understood to be a system made up of at least two components. Although reference to two components (i.e. paste A and paste B) is made in the following, the kit can just as well contain more than two components, for example three, four, five or more than five components, according to need. The individual components preferably are provided to be packaged separate from each other such that the ingredients of the one kit component do not contact the ingredients of another kit component. Accordingly, it is feasible, for example, to package the respective kit components separate from each other and to store them together in a reservoir container.

Preferably, the kit is designed as a kit for producing bone cement comprising a first container and a second container, whereby the first container comprises paste A and the second container comprises paste B, whereby at least one of the containers can be opened to allow for paste A and paste B to be mixed after the opening, and a mixing unit for the mixing of pastes A and B.

The components described above in the context of the paste according to the invention as preferred monomer for radical polymerisation, as polymer that is soluble in said monomer, as polymerisation initiator, as polymerisation accelerator, and as particulate inorganic filling agent are preferred as monomer (a1)) and/or (b1) for radical polymerisation, as polymer that is soluble in (a1)) and/or (b1), as polymerisation initiator (a3), as polymerisation accelerator (b3), and as particulate inorganic filling agent (a4) and/or (b4), respectively.

Preferably, paste A and paste B contain an amount of the at least one monomer for radical polymerisation (a1) and/or (b1) in a range of 15 to 85% by weight, more preferably 20 to 70% by weight, even more preferably 25 to 60% by weight, and particularly preferably 25 to 50% by weight, each relative to the total weight of paste A and/or paste B.

Preferably, paste A contains an amount of the polymerisation initiator (a3) in a range of 0.01 to 10% by weight, more preferably in a range of 0.01 to 8% by weight, and even more preferably in a range of 0.01 to 5% by weight, each relative to the total weight of paste A.

Provided the polymerisation accelerator (b3) is a heavy metal compound selected from the group consisting of heavy metal salts and heavy metal complexes, in particular is a heavy metal compound selected from the group consisting of copper(II) hydroxide, copper(II) methacrylate, copper(II) acetylacetonate, copper(II)-2-ethyl-hexanoate, cobalt(II) hydroxide, cobalt(II)-2-ethyl-hexanoate, basic copper(II) carbonate, iron(II)-2-ethyl-hexanoate, iron(III)-2-ethyl-hexanoate, and a mixture of at least two of these substances, paste B preferably contains an amount of said polymerisation accelerator (b3) in a range of 0.0005 to 0.5% by weight, relative to the total weight of paste B.

Provided the polymerisation accelerator (b3) is a compound selected from the group consisting of N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, 1,5-diazabicyclo(4.3.0)non-5-ene, phthalimide, maleimide, succinimide, pyromellitic acid diimide, and a mixture of at least two of these substances, paste B preferably contains an amount of said polymerisation accelerator (b3) in a range of 0.1 to 10% by weight, relative to the total weight of paste B.

Specifically, paste A can further contain as component (a5) the polymerisation co-accelerator described above, which preferably is a compound selected from the group consisting of N,N-dimethyl-p-toluidine, N,N-bis-hydroxyethyl-p-toluidine, N,N-dimethyl-aniline, 1,8-diazabicyclo[5.4.0]undec-7-ene, 1,5-diazabicyclo(4.3.0)non-5-ene, and a mixture of at least two of these substances. It is preferred in this context for paste A to contain an amount of the at least one polymerisation co-accelerator (a5) in a range of 0.1 to 10% by weight, relative to the total weight of paste A.

Provided one of the pastes of the kit according to the invention contains the poorly soluble or insoluble filling agent and the other paste contains no poorly soluble or insoluble filling agent at all or contains a negligible amount of poorly soluble or insoluble filling agent as compared to the amount present in the other paste, the kit is called "asymmetrical". In contrast, a so-called "symmetrical" kit has approximately comparable amounts of the poorly soluble or insoluble filling agent present in both pastes.

Moreover, pastes A and/or B can contain further additives aside from the components described above, such as radio-opaquers, colourants, pharmaceutical agents, biocompatible elastomers, monomers having adhesion groups or stabilisers, whereby the components described above, in the context of the paste according to the invention, as preferred radio-opaquers, colourants, pharmaceutical agents, biocompatible elastomers, monomers having adhesion groups, and stabilisers are preferred here as well.

According to a first particular refinement of the kit according to the invention, the kit is an "asymmetrical" kit. It is preferred in this context for paste A to contain 1 to 50% by weight, particularly preferably 1.0 to 15% by weight, even more preferably 30 to 55% by weight, and most preferably 1 to 5% by weight, each relative to the total weight of paste A, of the filling agent (a4) that is insoluble in (a1), and for paste B to contain less than 5% by weight, particularly preferably less than 1% by weight, even more preferably less than 0.1% by weight, and yet more preferably less than 0.01% by weight, each relative to the total weight of paste B, of the filling agent (b4) that is insoluble in (b1), whereby it is most preferred for paste B to contain no filling agent (b4) that is insoluble in (b1) at all.

Moreover, in the context of said first particular refinement of the kit according to the invention, it is preferred for paste A to contain an amount of the polymer (a2) that is soluble in (a1) in a range of 1 to 25% by weight, particularly preferably in a range of 2 to 20% by weight, even more preferably in a range of 2 to 18% by weight, and most preferably in a range of 3 to 16% by weight, each relative to the total weight of paste A, and for paste B to contain an amount of a polymer (b2) that is soluble in (b1) in a range of 25 to 85% by weight, particularly preferably in a range of 35 to 85% by weight, even more preferably in a range of 35 to 80% by weight, and most preferably in a range of 35 to 75% by weight, each relative to the total weight of paste B.

Moreover, it is preferred in the context of said first particular refinement of the kit according to the invention that the weight ratio of filling agent (b4) that is insoluble in (b1) to the at least one polymer (b2) that is soluble in (b1) is no more than 0.2, more preferably no more than 0.15, even more preferably no more than 0.1, yet more preferably no more than 0.05, particularly preferably no more than 0.02, and even more particularly preferably is equal to 0.

According to a second particular refinement of the kit according to the invention, the kit is a "symmetrical" kit. It is preferred in this context for paste A to contain 0.5 to 35% by weight, particularly preferably 0.5 to 15% by weight, and even more preferably 20 to 75% by weight, each relative to the total weight of paste A, of the filling agent (a4) that is insoluble in (a1), and for paste B to contain 0.5 to 35% by weight, particularly preferably 0.5 to 15% by weight, and even more preferably 0.5 to 5% by weight, each relative to the total weight of paste B, of the filling agent (b4) that is insoluble in (b1).

Moreover, in the context of said second particular refinement of the kit according to the invention, it is preferred that paste A contains an amount of a polymer (a2) that is soluble in (a1) in a range of 5 to 50% by weight, particularly preferably in a range of 10 to 40% by weight, and even more preferably in a range of 20 to 30% by weight, each relative to the total weight of paste A, and/or paste B contains an amount of a polymer (b2) that is soluble in (b1) in a range of 5 to 50% by weight, particularly preferably in a range of 10 to 40% by weight, and even more preferably in a range of 20 to 30% by weight, each relative to the total weight of paste B.

According to the invention, the purpose of the paste and/or kit according to the invention containing at least pastes A and B is the production of bone cement.

Referring to the kit, for this purpose, the at least two pastes A and B are mixed with each other, upon which another paste, paste C, is obtained. The mixing ratio preferably is 0.5 to 1.5 parts by weight of paste A and 0.5 to 1.5 parts by weight of paste B. According to a particularly preferred embodiment, the fraction of paste A is 30 to 70% by weight and the fraction of paste B is 30 to 70% by weight, each relative to the total weight of pastes A and B, respectively. Mixing can be effected with common mixing devices, for example a static mixer or a dynamic mixer.

After mixing the pastes of the kit, paste C which is ultimately obtained (and corresponds to the paste according to the invention specified above) is tack-free in accordance with the ISO 5833 standard no later than after 15 minutes.

The bone cement generated from paste C by curing attains high strength approximately six to eight minutes after mixing the pastes contained in the kit.

According to a preferred embodiment, paste C and/or the kit according to the invention can be used for mechanical fixation of articular endoprostheses, for covering skull defects, for filling bone cavities, for femuroplasty, for vertebroplasty, for kyphoplasty, for the manufacture of spacers, and for the production of carrier materials for local antibiotics therapy.

In this context, the term, "spacer", shall be understood to mean implants that can be used temporarily as spacer in the scope of the two-step exchange of prostheses in septic revision surgeries.

Carrier materials for local antibiotics therapy can be provided as spheres or sphere-like bodies or as bean-shaped bodies. Besides, it is also feasible to produce rod-shaped or disc-shaped carrier materials that contain the bone cement made from the paste according to the invention and/or the kit according to the invention. Moreover, the carrier materials can also be threaded onto absorbable or non-absorbable suture material in a bead-like manner.

The uses according to the invention of bone cement described above are known from the literature and have been described therein on numerous occasions.

A contribution to meeting the objects specified above is also made by a form body that is obtainable through polymerisation of a paste that is obtainable through mixing paste A and paste B of the kit according to the invention or through polymerisation of a paste according to the invention. Form bodies according to the scope of the present invention can be any three-dimensional bodies, in particular the "spacers" described above.

The invention shall be illustrated through the examples described in the following, though without limiting the scope of the invention.

Exemplary Embodiments

Pastes A of examples A1-6 were produced by simply mixing the components. The pastes thus formed were then stored over night at room temperature.

Paste A

| Example no. | CH [mg] | BH [g] | DM [g] | EG [g] | MA [g] | MMA [g] | PL1 [g] | AE [g] | ZrO₂ [g] | Rod [mg] |
|---|---|---|---|---|---|---|---|---|---|---|
| A1 | 75 | 2.00 | — | — | — | 14.00 | 6.00 | 2.00 | 20.00 | 20 |
| A2 | 50 | 1.80 | 0.20 | — | — | 14.00 | 7.00 | 1.50 | 20.00 | 20 |
| A3 | 50 | 1.80 | 0.20 | 0.50 | — | 13.50 | 7.00 | 1.00 | 20.00 | 20 |
| A4 | 50 | 1.90 | 0.10 | — | — | 14.00 | 6.00 | 1.50 | 20.00 | 20 |
| A5 | 50 | 1.40 | 0.60 | 0.10 | 0.40 | 17.70 | 13.60 | 1.00 | 4.80 | 20 |
| A6 | 50 | 1.40 | 0.60 | 0.10 | 0.40 | 17.70 | 13.60 | 2.00 | 4.80 | 20 |

CH: Cumene hydroperoxide
BH: N,N-Bis-(2-hydroxyethyl)-p-toluidine
DM: N,N-Dimethyl-p-toluidine
EG: Ethylene glycol dimethacrylate
MA: Methacrylamide
MMA: Methylmethacrylate
PL1: linear poly(methylmethacrylate-co-methylacrylate) MW <500,000 g/mol
AE: Aerosil ® 380 (pyrogenic silicic acid)
ZrO₂: Zirconium dioxide
Rod: 2,6-Di-t-butyl-4-methyl-phenol Pastes B of examples B1-6 were produced by simply mixing the components. The pastes thus formed were then stored over night at room temperature.

Paste B

| Example no. | SAC [g] | CuOct [mg] | MMA [g] | PL1 [g] | AE [g] | Rod [mg] |
|---|---|---|---|---|---|---|
| B1 | 1.00 | 55 | 22.00 | 18.00 | — | 35 |
| B2 | 1.00 | 55 | 23.00 | 17.00 | — | 35 |
| B3 | 1.00 | 55 | 23.00 | 17.00 | — | 35 |
| B4 | 1.00 | 55 | 22.00 | 18.00 | 0.50 | 35 |
| B5 | 1.00 | 55 | 21.20 | 17.50 | — | 35 |
| B6 | 1.00 | 55 | 21.20 | 17.50 | — | 35 |

SAC: Saccharine
CuOct: Copper(II)-2-ethylhexanoate
MMA: Methylmethacrylate
PL1: linear poly(methylmethacrylate-co-methylacrylate), MW <500,000 g/mol
AE: Aerosil ® 380 (pyrogenic silicic acid)
Rod: 2,6-Di-t-butyl-4-methyl-phenol The pastes A and B of examples A1-6 and B1-6 were mixed with each other at a weight ratio of 1:1. This produced pastes C that were tack-free right away and, in the case of pastes C1 to C4, had a processing time of up to 20 minutes. During the processing phase, it was feasible to force said pastes through 18 G cannulas (cannula with an external diameter of 1.2 mm) without any difficulty.

In contrast, the viscosity and the processing phase of pastes C5 and C6 were similar to conventional high viscosity polymethylmethacrylate bone cements. The processing phase lasted for 4-5 minutes.

The mixed pastes C produced from pastes A and B of examples 1-6 (weight ratio of paste A to paste B of 1:1) were used to produce strip-shaped test bodies with dimensions of (75 mm×10 mm×3.3 mm) for the assay of bending strength and flexural modulus and cylindrical test bodies (diameter 6 mm, height 12 mm) were used for the assay of compressive strength. The test bodies were then stored for 24 hours on air at 23±1° C. Then the 4-point flexural strength, flexural modulus, and the compressive strength of the test bodies were determined using a Zwick universal testing device.

| Pastes C | Compositions of Pastes C | 4-point flexural strength [MPa] | Flexural modulus [MPa] | Compressive strength [MPa] |
|---|---|---|---|---|
| C1 | A1 + B1 | 57.9 ± 0.7 | 2686 ± 51 | 102.0 ± 2.4 |
| C2 | A2 + B2 | 58.9 ± 0.4 | 2643 ± 53 | 96.5 ± 4.1 |
| C3 | A3 + B3 | 58.7 ± 1.9 | 2682 ± 153 | 94.4 ± 4.3 |
| C4 | A4 + B4 | 62.9 ± 1.7 | 2927 ± 91 | 92.2 ± 6.2 |
| C5 | A5 + B5 | 58.1 ± 1.4 | 2405 ± 77 | 91.2 ± 4.4 |
| C6 | A6 + B6 | 60.1 ± 3.1 | 2561 ± 192 | 93.9 ± 3.3 |

The results of the 4-point flexural strength, flexural modulus, and compressive strength tests on cured pastes C1-6 show that the mechanical stability requirements of ISO 5833 are met. ISO 5833 defines the following parameters: 4-point flexural strength of at least 50 MPa, flexural modulus of at least 1,800 MPa, and compressive strength of at least 70 MPa.

Moreover, additional pastes B that were produced analogous to paste B6 except that each had 1.0 g vancomycin hydrochloride, clindamycin hydrochloride, daptomycin, and octenidine dihydrochloride, and gentamicin sulfate added. After mixing these pastes B with paste A1 at a weight ratio of 1:1, the mixed pastes C showed a similar curing behaviour as the combination of paste A6 and paste B6 at a weight ratio of 1:1.

In addition, pastes were produced using barium sulfate instead of zirconium dioxide. Said pastes had a similar curing behaviour as the pastes C1-6 produced from pastes A1-6 and B1-6.

Furthermore, pastes A were produced analogous to example A1, but using t-butyl-hydroperoxid, t-amyl-hydroperoxide, and dicumyl-peroxide instead of cumene-hydroperoxide. After mixing these pastes A with paste B1 at a weight ratio of 1:1, the mixed pastes showed a similar behaviour as the combination of pastes A1 and paste B1.

The invention claimed is:
1. Paste consisting of at least one monomer for radical polymerization, selected from the group consisting of methacrylic acid methylester, methacrylic acid ethylester and a mixture of said two monomers, at least one polymer that is soluble in said at least one monomer for radical polymerization, and at least one particulate inorganic filling agent that is poorly soluble or insoluble in said at least one monomer for radical polymerization, said at least one par- ticulate inorganic filling agent being selected from the group consisting of pyrogenic silicon dioxide, pyrogenic silicon dioxide made hydrophobic, pyrogenic metal-silicon oxides, titanium dioxide, bentonite, montmorillonite, and a mixture of at least two of these substances,
- optionally at least one x-ray opaquer selected from the group consisting of metal oxides, barium sulfate, toxicologically acceptable heavy metal particles, ferrite, and magnetite and biocompatible calcium salts,
- at least one initiator,
- optionally at least one accelerator,
- optionally at least one heavy metal compound selected from the group consisting of copper(II) hydroxide, copper(II) methacrylate, copper(II) acetylacetonate, copper(II)-2-ethyl-hexonate, cobalt(II) hydroxide, cobalt(II)-2-ethylhexonate, basic copper(II) carbonate, iron(II)-2-ethyl-hexyl-hexonate, iron(III)-2-ethyl-hexonate, and a mixture of at least two of these substances,
- optionally at least one co-accelerator,
- optionally at least one colorant,
- optionally at least one pharmaceutical agent,
- optionally at least one biocompatible elastomer,
- optionally at least one monomer having adsorption groups, and
- optionally at least one stabilizer, wherein the filling agent is a particulate inorganic filling agent possessing a BET surface of at least 40 $m^2/g$.

2. Paste according to claim 1, whereby the particulate inorganic filling agent comprises hydroxy groups that are bound covalently to the particles.

3. Paste according to claim 2, wherein the particulate inorganic filling agent comprises HO—Si groups (silanol groups) that are bound covalently to the particles.

4. Paste according to claim 1, wherein the particulate inorganic filling agent is pyrogenic silicon dioxide with a BET surface of at least 200 $m^2/g$.

5. Paste according to claim 4, wherein the particulate inorganic filling agent is pyrogenic silicon dioxide with a BET surface of at least 300 $m^2/g$.

6. Paste according to claim 1, wherein the paste contains 0.5 to 25% by weight, relative to the total weight of the paste, of the particulate inorganic filling agent.

7. Paste according to claim 1, wherein the paste contains, in addition, at least one polymerization initiator, at least one polymerization accelerator, and optionally at least one polymerization co-accelerator.

8. Paste according to claim 1, wherein the soluble polymer is selected from the group consisting of poly(methacrylic acid methylester), poly(methacrylic acid ethylester), poly(methylmethacrylic acid propylester), poly(methacrylic acid isopropylester), poly(methylmethacrylate-co-methylacrylate), poly(styrene-co-methylmethacrylate), and a mixture of at least two of said polymers.

9. Paste according to claim 1, wherein the paste is tack-free in accordance with ISO 5833 no later than 15 minutes after being produced.

10. A method for mechanical fixation of articular endoprostheses, for covering skull defects, for filling bone cavities, for femuroplasty, for vertebroplasty, for kyphoplasty, for the manufacture of spacers or for the production of carrier materials for local antibiotics therapy by application of a paste of claim 1.

11. Form body obtained through polymerization of a paste of claim 1.

* * * * *